(12) United States Patent
Bedoukian et al.

(10) Patent No.: US 9,021,738 B2
(45) Date of Patent: May 5, 2015

(54) CONTROL OF TERMITES, FIRE ANTS AND CARPENTER ANTS

(75) Inventors: Robert H. Bedoukian, West Redding, CT (US); Ashok Raina, Ellicott City, MD (US)

(73) Assignee: Bedoukian Research, Inc., Danbury, CT (US)

( * ) Notice: Subject to any disclaimer, the term of this patent is extended or adjusted under 35 U.S.C. 154(b) by 177 days.

(21) Appl. No.: 12/998,515

(22) PCT Filed: Nov. 2, 2009

(86) PCT No.: PCT/US2009/005926
§ 371 (c)(1),
(2), (4) Date: Apr. 28, 2011

(87) PCT Pub. No.: WO2010/062368
PCT Pub. Date: Jun. 3, 2010

(65) Prior Publication Data
US 2011/0203160 A1     Aug. 25, 2011

Related U.S. Application Data

(60) Provisional application No. 61/198,092, filed on Nov. 3, 2008.

(51) Int. Cl.
A01M 1/20 (2006.01)
A01N 35/06 (2006.01)

(52) U.S. Cl.
CPC .................................. *A01N 35/06* (2013.01)

(58) Field of Classification Search
USPC ................................................. 43/124, 132.1
See application file for complete search history.

(56) References Cited

U.S. PATENT DOCUMENTS

| | | | |
|---|---|---|---|
| 4,906,488 A * | 3/1990 | Pera | 426/573 |
| 4,993,639 A * | 2/1991 | Hata | 239/289 |
| 6,581,324 B1 | 6/2003 | Creeger et al. | 43/131 |
| 8,137,715 B2 * | 3/2012 | Shah et al. | 424/776 |
| 2007/0049644 A1 * | 3/2007 | Bedoukian et al. | 514/690 |
| 2008/0193387 A1 * | 8/2008 | De Wolff | 424/47 |
| 2009/0263511 A1 * | 10/2009 | Shah et al. | 424/725 |
| 2010/0144888 A1 * | 6/2010 | Bessette | 514/690 |
| 2011/0203160 A1 * | 8/2011 | Bedoukian et al. | 43/124 |
| 2011/0213038 A1 * | 9/2011 | Bedoukian | 514/678 |

FOREIGN PATENT DOCUMENTS

WO    WO 0021364 A2 *  4/2000

* cited by examiner

*Primary Examiner* — Christopher P Ellis
(74) *Attorney, Agent, or Firm* — Ohlandt, Greeley, Ruggiero & Perle, L.L.P.

(57) ABSTRACT

D- and l-tetrahydrocarvone and d- and l dihydrocarvone are effective for the control of termites, fire ants and carpenter ants.

16 Claims, No Drawings

CONTROL OF TERMITES, FIRE ANTS AND CARPENTER ANTS

CROSS-REFERENCE TO RELATED APPLICATIONS

This application is a 371 of International Application No. PCT/US2009/005926, which was filed on Nov. 2, 2009, which is in turn based upon and claims the benefit of priority from U.S. Provisional Application No. 61/198,092, filed Nov. 3, 2008, the entire contents of each of which are incorporated herein by reference.

FIELD OF THE INVENTION

The invention relates to improved pesticidal chemicals and pesticidal compositions of naturally occurring compounds and methods of using same for control of Formosan and other subterranean termites, imported fire ants and carpenter ants, particularly employing such compositions of naturally occurring compounds and methods to control termites, fire ants and carpenter ants with pesticidal compositions effective by both vapor transmission and also effective against termites, fire ants and carpenter ants when they are found in soil and/or wood environments.

BACKGROUND TO THE INVENTION

Subterranean termites in general and the Formosan subterranean termite (FST) in particular are very serious urban pests not only in the United States but also in many countries throughout the world. In the United States, in addition to the native subterranean termites, several southern states and Hawaii are infested with the exotic Formosan subterranean termite (FST), *Coptotermes formosanus* Shiraki (Isoptera: Rhinotermitidae). In addition to infesting wooden structures the FST also infects live trees. Established colonies of foraging subterranean termites, for example *Reticulitermes* spp and *Coptotermes formosanus*, are difficult to control. These termites are known to cause colossal destruction of human property resulting in great economic loss. These termites are known to cause an estimated two billion dollars in preventive control, damage and repair costs each year.

The subterranean habitat of such termites makes it very difficult to treat infestation sites with conventional insecticides. It has become increasingly apparent that widespread use of synthetic chemical pesticides has caused detrimental environmental effects that are harmful to humans. Residual pesticides have been found in food, ground water and throughout the environment. Many of these pesticides are toxic or carcinogenic or are otherwise detrimental to humans and animals as well as fish. The inventory of conventional insecticides is greatly reduced because of stricter restrictions and regulatory guidelines based on environmental concerns and safety measures. Currently, baits containing chitin synthesis inhibitors (which disrupt molting), is the main tool used for termite control. In spite of being effective, it has two drawbacks; the termites have to first find the bait and additionally the process of colony elimination may take anywhere up to three months. The latter projection is based on the fact that only about 1% of the termite workers in a colony molts each day.

The previously referred to regulatory guidelines have encouraged a search for potentially less dangerous pesticides by restricting the use of certain synthetic pesticides or elimination of certain effective pesticides from the marketplace and reduced the ability to control pests. Therefore, natural products have become of possible interest because they are generally safer to humans and the environment than synthetic pesticides. Some natural products, particularly those that are volatile, have been studied for termite control (Wilkins, Mater. Org. 27: 47-65 (1992); Bläske and Hertel, J. Econ. Entomol. 94: 1200-1208 (2001); Tellez et al., Sociobiology 41: 153-167 (2003); Park and Shin. J. Agric. Food Chem. 53: 4388-4392 (2005); Raina et al., J. Econ. Entomol. 100: 880-885 (2007). Cornelius et al., J. Econ. Entomol. 90: 320-325 (1997) determined the toxicity of monoterpenoids and other natural products to *C. formosanus* in test tubes containing sand treated with these compounds. However, in most cases tests were carried out in Petri dishes, which do not take into account the cryptic nature of subterranean termites. Many a time very high doses have been used to demonstrate efficacy of a chemical. As example, Bessette U.S. Pat. No. 6,858, 653 claims that about 28 mg (example 1) of several plant essential oils, applied to glass Petri dishes, killed 100% of drywood termites in 1 hr. It is also to be noted that these tests involved potential physical contact with the test substances, and were performed in an environment that does not simulate the natural soil and wood environment of the FST. Whereas, some of the plant essential oil components, such as carveol, citronellal, p-cymene and geraniol, were claimed to cause high mortality of drywood and other termites in Petri dish assays, we found them to be totally ineffective against termites in soil and wood.

Current termite management practices include the use of baits placed around properties to be protected. A major drawback of the baits is that termites have to first find these baits and the treatments are costly and often time consuming In the southern United States, fire ants *Solenopsis invicta*, are a significant pest. For example, foraging fire ants are known to destroy young citrus trees, growing crops, and germinating seeds. Fire ants are omnivorous, feeding on almost any plant or animal matter and they damage young plants by gnawing holes in roots, tubers, stalks, and buds. The fire ant population has increased so rapidly that they are responsible for the major destruction of crops such as soybeans, potatoes and other vegetables in the farming regions of the United States where they have taken over. They have had a major impact on ground nesting animals and they are a menace to both humans and domestic animals alike. Their venom can cause health problems for humans who are hypersensitive to their venom. For a great number of years there has been a need to control the spread of black and red imported fire ants that are invading ever-increasing areas of the United States. With each passing year they spread further north, east and west affecting more States and causing hundreds of million dollars worth of damage per year.

One approach to control fire ant has been to employ synthetic chemical pesticides, but these have met very limited success. Moreover, these synthetic chemical pesticides can also pose grave environmental hazards. Federal agencies of the US government have imposed restrictions on some chemicals in an effort to protect the environment from the harmful toxic effects produced by these chemicals. Among the chemicals banned or restricted in use by governments are: DDT, Chlorodane, Lindane, Aldrin, Heptechlor, Dieldrin, and Mirex. Mirex (perchloropentacyclodecane) was found to be one of the most effective fire ant killers, however since its use has been banned in the United States because it has been found to be a, bioaccumulative, and toxic pollutant, the fire ant population has increased rapidly.

There are still a number of commercial pesticide products on the market currently. These pesticides are typically contact poisons and are effective in killing a wide variety of insects.

One which specifically targeted fire ants is the AMDRO® a hydramethylnon-based hydrazone insecticide product (trademark of Central Garden & Pet Company Corporation). This product is a delayed-action pesticide advertised to be effective against fire ants because it is eventually ingested by the queen. When the queen is killed, the colony vanishes and the mound is destroyed. However, AMDRO has a number of drawbacks. AMDRO loses much of it's effectiveness following contact with moisture. This is a serious shortcoming, since much of the domain of imported fire ants is along the southern coastal states of the United States where rainfall is plentiful. AMDRO also has a short shelf life after the container has been opened.

Fire ants have a significant economic impact on agriculture in infested areas. Additionally, telecommunication companies spend substantial amounts of money each year on treating their electrical equipment to prevent fire ant invasion because fire ants are attracted to electrical fields and can short out electrical equipment. Moreover, farm equipment can be damaged by large fire ant mounds. Fire ants also present a problem to wildlife, such as with ground nesting birds and animals. Furthermore, Fire ants are known to excavate the soil from under roadways causing damage.

Fire ants also pose a health care problem to the millions of people that are stung by them. Since a significant number of those people require medical care. Additionally it has been reported that fire ant stings are also blamed for human deaths each year. Thus, because of the problem fire ants present there is increasingly greater interest in controlling these fire ants.

This interest has resulted in much research and resources being expended through the years to develop compositions and methods for controlling fire ants. One type of desirable composition which would be of great interest would be a non-toxic naturally occurring reagent which could repel, or keep ants from invading a particular area or object.

Current methods for controlling structural infestations of carpenter ants include sanitation of potential and current nest sites, minimizing access to structures (e.g., preventing the contact of tree branches with a structure), and the application of insecticides to repel (perimeter spray barriers) and/or eliminate carpenter ants. The use of boric acid dust in dry, wall voids is reported to be effective for up to 20 years (Hansen and Akre, supra).

Recommendations for the chemical control of established structural infestations in the home are often accompanied with warnings of possible hazards to the applicator as well as children and pets. Alternative control methods such as effective biological control agents have not been found (Akre, R. D., L. D. Hansen, A. L. Antonelli [1989] Ext. Bull. Washington State Univ. Coop. Ext. Serv. 1989 rev. no. EB 0818, 6 pp.). A need clearly exists for a safe, effective biological control agent for carpenter ants.

One aspect of the present invention is to provide significantly effective compositions or formulations of naturally occurring compounds, particularly effective at significantly low concentrations, and chemicals therefor that are able to control and kill termites not only by vapors that can be carried by air to a target site to control or kill the termites but that can effectively penetrate wood and soil environments where the termites are found so as to control and kill them within that environment. Another aspect of this invention is to provide significantly effective compositions or formulations of naturally occurring compounds, particularly effective at significantly low concentrations, and chemicals therefor that are able to control and kill fire and carpenter ants not only by vapors that can be carried by air to a target site to control or kill the fire ants but that can effectively penetrate soil environments where the fire ants are found so as to control and kill them within that environment. A further aspect of the invention is to provide significantly effective compositions or formulations of naturally occurring compounds, particularly effective at significantly low concentrations, and chemicals therefor that are able to control and kill both termites and fire and carpenter ants. Yet another aspect of this invention is to provide such significantly effective compositions or formulations of naturally occurring food grade compounds, particularly effective at significantly low concentrations that are both effective against fire and carpenter ants and termites and at the same time is generally non-toxic to humans, biodegradable and considered to be environmentally safe.

SUMMARY OF THE INVENTION

In one aspect of the invention control of termites and fire and carpenter ants has been achieved with the use of compositions or formulations containing at least one of the naturally occurring compounds dihydrocarvone and tetrahydrocarvone, including both the d- and l-forms thereof. The use of the compounds dihydrocarvone and tetrahydrocarvone to control termites and fire and carpenter ants has been found to be effective by contact with the pests, by contact of the pests with vapor mist of these compounds, and by vapors of these compounds released in soil and wood environments where these pests are found. These compounds have been found to produce generally at least about 75% mortality within 24 hours, and particularly about 100% mortality within 48 hours of the termites or fire and carpenter ants encountering these compounds in the aforementioned environments. Any effective amount of one or more of these compounds may be employed in control of the termites and fire and carpenter ants. The effective control compounds of this invention may also be employed with other know pesticides where desirable. A further aspect of this invention is to a method for control of termites or fire and carpenter ants that involves the application of compositions or formulations at least one of compounds dihydrocarvone and tetrahydrocarvone to an environment where these pests are likely to be found, including soil and wooded environments.

DETAILED DESCRIPTION OF THE INVENTION

Control of termites and fire and carpenter ants has been achieved with the use of compositions or formulations containing at least one of the naturally occurring compounds dihydrocarvone and tetrahydrocarvone, including both the d- and l-forms thereof. The use of the compounds dihydrocarvone and tetrahydrocarvone to control termites and fire and carpenter ants has been found to be particularly effective by contact with the pests, by contact of the pests with vapor mist of these compounds, and by vapors of these compounds released in soil and wood environments where these pests are found. These compounds have been found to produce generally at least about 75% mortality within 24 hours, and particularly about 100% mortality within 24 hours of the termites or fire and carpenter ants encountering these compounds in the aforementioned environments. Any effective amount of one or more of these compounds may be employed in control of the termites and fire and carpenter ants. The effective control compounds of this invention may also be employed with other know pesticides where desirable. Additionally, according to an embodiment of this invention a method for control of termites or fire and carpenter ants involves the application of compositions or formulations of at least one of compounds dihydrocarvone and tetrahydrocarvone to an environment where these pests are likely to be found, including soil and wooded environments.

The compounds dihydrocarvone and tetrahydrocarvone may be employed in any suitable concentration producing acceptable control of termites and fire and carpenter ants. Such control effective vapor concentration can be, but is not limited to, a concentration amount of from about 25 to about 600 ppm, more preferably in a concentration of from about 50 to about 400 ppm and even more preferably in a concentration of from about 100 to about 300 ppm as limited by their vapor pressure at the ambient temperature. A particularly desirable concentration for dihydrocarvone and tetrahydrocarvone for contact is about 1% on the contact surface.

The compounds dihydrocarvone and tetrahydrocarvone may be employed in any suitable vehicle or carrier, including, but not limited to carriers such as vegetable oil, propylene glycol, organic solvents, aqueous solutions or emulsions, absorbent material of any type, or dissolved in plastics. A further exemplary means of using the pesticidally effective dihydrocarvone and tetrahydrocarvone is to introduce such compounds into the nest of the pests when the pests are located behind a barrier wall. For example, such a method may comprise the following exemplary, but not limiting method. Such exemplary method may comprise locating the nest of the pests, e.g., termites, that is behind a barrier wall, such as by infrared thermography, moisture measurements, microwaves, acoustical means or the like, then providing one or more small holes in the barrier wall adjacent to the nest and into the nest such as by drilling or the like, and then introducing, such as by injecting, a pesticidally effective amount of the at least one of the toxicant compound selected from dihydrocarvone and tetrahydrocarvone into the nest by way of the one or more holes. The toxicant compound may be introduced into the nest either as the toxicant compound per se, or in an absorbent material or plastic matrix or as a solution in a suitable carrier vehicle such as propylene glycol-water mixtures.

The following test methods and assays were employed that demonstrate the usefulness of dihydrocarvone and tetrahydrocarvone for the control of termites and fire and carpenter ants.

Formosan subterranean termites were collected from bucket traps placed in City Park, New Orleans, La. Altogether five colonies designated 1314, 1559, 1732, 1743 and 1756 were used in the tests. After collection, the termites (primarily workers and soldiers) were transferred to plastic boxes with moist spruce slats. The boxes were stored in an incubator maintained at 28° C., 65% RH, and constant darkness. Termites were used within one month of their collection.

Assay for Contact Toxicity. The assay was conducted in 55 by 15 mm plastic Petri dishes. Initially, 22 chemicals were tested at 1.0%. Then the test chemicals were dissolved in 95% ethanol and 100 µl of the solution applied to 4.25-cm-diameter filter papers (approximate wt. 100 mg) to obtain concentrations of 1.0, 0.5 and 0.1% w/w {relative to the filter paper}. After allowing the solvent to evaporate, the filter paper was moistened with 180 µl distilled water. Twenty workers were released into each Petri dish and all the dishes with one treatment were placed in secondary containers (to prevent desiccation of termites). Each chemical was tested with 3 colonies and replicated 4 times. All the containers were kept at 28° C. and constant darkness. Mortality was recorded after 1, 3, 5 and 7 days.

Assay for Vapor Toxicity. This test was conducted in 960 ml wide-mouth clear Qorpak™ (All-Pak, Inc.) bottles with PTFE lined caps. A 60 mm diameter glass Petri dish with a moist filter paper and 50 termite workers was placed at the bottom of each bottle. The test chemical was applied to a 1 cm diameter filter paper and suspended with an insect pin from the cap-liner. Each chemical was initially tested at 1 mg in the one liter bottle then at 0.1 and 0.5 mg. Since 0.1 and 0.5 mg doses caused very low and 100% mortality respectively, the final test was carried out at 0.25 mg. Each chemical was tested with different termite colonies and replicated three times. The bottles were placed in the incubator. Mortality was recorded after 1, 2 and 3 days by quickly taking the glass Petri dish with the termites out of the bottle (with a pair of long forceps) and replacing it after removing the dead workers.

Vapor Toxicity Under Subterranean Conditions. This test was also conducted in the one liter Qorpak™ bottles. A 35 by 40 by 7 mm piece of moist spruce was placed at the bottom of the bottle and covered with 40 g fine-sifted black soil. One hundred termite workers were released into each bottle and allowed to tunnel under the soil and into the wood. After 3 days, a test chemical was applied to a filter paper and suspended from the cap-liner. The chemicals were tested at 10, 25 and 50 mg. Mortality was recorded after 2 days. The test was conducted with termites from 3 colonies and replicated 3 times.

The same Vapor Toxicity Under Subterranean Conditions test as described in paragraph [0023] was conducted except that fire ants were employed instead of termites.

In the vapor toxicity testing tetrahydro-l-carvone and tetrahydro-d-carvone each killed 100% of the termites in 1 day at when employed at a level of 1 mg per liter volume and tetrahydro-d-carvone killed 100% of the termites in 1 day at when employed at a concentration of 0.5 mg/liter volume and 75% of the termites in 3 days when employed at a concentration of 0.25 mg/liter volume.

In the vapor toxicity under subterranean conditions testing tetrahydro-l-carvone killed 100% of the termites in 24 hrs and dihydro-l-carvone killed 100% of the termites in 48 hours when employed at a rate of 25 mg/liter volume. It should be noted that the vapor pressures of these materials limit the amount of test substance in the air to approximately 100-250 ppm, and that only approximately 1 mg of test substance is actually be in the vapor state.

Because in their natural environment the subterranean termites are not expected to be exposed to a chemical in open space, we conducted the next test by placing 100 workers termites in spruce slats covered with a layer of soil, all placed in the same glass bottles. Tests were conducted at 25 mg dose. After 2 days tetrahydrocarvone (both d- and l-isomers) caused 100% mortality.

In the vapor toxicity under subterranean conditions testing tetrahydro-d-carvone and tetrahydro-l-carvone both killed 100% of the fire ants in 24 hours at a rate of 25 mg.

One drop (approximately 30 mg) of tetrahydro l-carvone test compound was applied to filter paper within a sealed jar (16 oz glass jar, 3½ inch diameter, 3⅞ inch high with plastic lids) containing ten carpenter (*Camponotus chromaoides*) ants per replicate with there being five replicates. Five negative controls with no test compounds were also run. The tetrahydro-l-carvone provided 100% mortality to the carpenter ants within 24 hours while the control produced 6% mortality over the same 24 hour period.

While the invention has been described herein with reference to the specific embodiments thereof, it will be appreciated that changes, modification and variations can be made without departing from the spirit and scope of the inventive concept disclosed herein. Accordingly, it is intended to embrace all such changes, modification and variations that fall with the spirit and scope of the appended claims.

We claim:

1. A method for the control of pests selected from termites, fire ants and carpenter ants in an area comprising application to an environment where it is desired to control at least one of these pests a pesticidally effective amount of tetrahydrocarvone; wherein application of the at least one compound results in at least about 75% mortality in about 24 hour of the pest desired to be controlled.

2. The method according to claim 1 wherein the compound is selected from tetrahydro d-carvone and tetrahydro-l-carvone.

3. The method according to claim 1 wherein the pests to be controlled are termites.

4. The method according to claim 3 wherein the termites are Formosan subterranean termites.

5. The method according to claim 3 wherein the compound is employed in an area that comprises an area selected from wood, soil, and mixtures of wood and soil.

6. The method according to claim 1 wherein the pests to be controlled are fire ants.

7. The method according to claim 1 where application of the at least one compound results in up to a 100% mortality in about 48 hours of the pest desired to be controlled.

8. The method according to claim 1 wherein at least one of the pest to be controlled are located in a nesting area behind a barrier wall, and the method comprises locating the nest of the pests, providing one or more holes in the barrier wall adjacent the nest and into the nest, and introducing the pesticidally effective amount of tetrahydrocarvone into the nest by way of the one or more holes.

9. The method according to claim 8 wherein the pests to be controlled are termites.

10. A composition for control of pests selected from termites, fire ants and carpenter ants that comprises a carrier vehicle and tetrahydrocarvone present in the composition in an amount sufficient to be released from the carrier vehicle in a pesticidally effective amount for said termites, fire ants and carpenter ants; wherein application of the composition results in at least about 75% mortality in about 24 hours of the pest desired to be controlled.

11. The composition according to claim 10 wherein the compound is selected from tetrahydro d-carvone and tetrahydro-l-carvone.

12. The composition according to claim 10 wherein the pests to be controlled are termites.

13. The composition according to claim 12 wherein the termites are Formosan subterranean termites.

14. The method for the control of pests selected from termites, fire ants and carpenter ants in an area consisting essentially of application to a soil or wood environment, where it is desired to control at least one of these pests, a pesticidally effective amount of tetrahydrocarvone to produce in the environment a vapor mist concentration of tetrahydrocarvone of from about 25 to about 600 ppm, wherein application of the tetrahydrocarvone results in at least about 75% mortality in about 48 hours of the pest desired to be controlled.

15. The method according to claim 14 wherein the pest is selected from Formosan subterranean termites and the application of the vapor mist of tetrahydrocarvone results in about 100% mortality of the Formosan subterranean termites.

16. The method according to claim 1 consisting essentially of application to a soil or wood environment, where it is desired to control at least one of the pests, a pesticidally effective amount of tetrahydrocarvone to produce in the environment a vapor mist concentration from about 25 to about 600 ppm of tetrahydrocarvone and wherein application of the vapor mist of tetrahydrocarvone results in about 100% mortality of the pest to be controlled.

* * * * *